United States Patent
Hofer et al.

(10) Patent No.: US 11,540,946 B2
(45) Date of Patent: Jan. 3, 2023

(54) PROCESS MONITORING AND CONTROL DURING LASER-BASED REFRACTIVE INDEX MODIFICATION OF INTRAOCULAR LENSES IN PATIENTS

(71) Applicant: AMO Development, LLC, Irvine, CA (US)

(72) Inventors: Richard Hofer, Santa Cruz, CA (US); Alexander Vankov, Mountain View, CA (US); Jenny Wang, Mountain View, CA (US); David A. Dewey, Sunnyvale, CA (US); Phillip Gooding, Mountain View, CA (US); Georg Schuele, Portola Valley, CA (US)

(73) Assignee: AMO Development, LLC, Irvine, CA (US)

( * ) Notice: Subject to any disclaimer, the term of this patent is extended or adjusted under 35 U.S.C. 154(b) by 0 days.

(21) Appl. No.: 17/057,689

(22) PCT Filed: Apr. 7, 2020

(86) PCT No.: PCT/IB2020/053327
§ 371 (c)(1),
(2) Date: Nov. 22, 2020

(87) PCT Pub. No.: WO2020/208531
PCT Pub. Date: Oct. 15, 2020

(65) Prior Publication Data
US 2022/0015948 A1  Jan. 20, 2022

Related U.S. Application Data

(60) Provisional application No. 62/925,185, filed on Oct. 23, 2019, provisional application No. 62/832,797, filed on Apr. 11, 2019.

(51) Int. Cl.
*A61F 9/008* (2006.01)
*A61L 27/16* (2006.01)
*A61B 17/00* (2006.01)

(52) U.S. Cl.
CPC ...... *A61F 9/00827* (2013.01); *A61F 9/00834* (2013.01); *A61L 27/16* (2013.01);
(Continued)

(58) Field of Classification Search
CPC ........ A61F 9/00834; A61F 2009/00844; A61F 2009/00851; A61F 2009/00897
See application file for complete search history.

(56) References Cited

U.S. PATENT DOCUMENTS

| 8,845,625 B2 | 9/2014 | Angeley et al. |
| 2009/0036880 A1* | 2/2009 | Bischoff ............... A61F 2/1627 606/13 |
| 2010/0069894 A1* | 3/2010 | Mrochen ................ A61F 9/008 606/4 |

(Continued)

FOREIGN PATENT DOCUMENTS

| WO | 2011109039 A1 | 9/2011 |
| WO | 2012166696 A1 | 12/2012 |
| WO | 2013162879 A1 | 10/2013 |

OTHER PUBLICATIONS

International Search Report and Written Opinion for Application No. PCT/IB2020/053327, dated Jun. 9, 2020, 13 pages.

*Primary Examiner* — Nathan J Jenness
(74) *Attorney, Agent, or Firm* — Johnson & Johnson Surgical Vision, Inc.

(57) ABSTRACT

Methods and related apparatus for real-time process monitoring during laser-based refractive index modification of an intraocular lens. During in situ laser treatment of the IOL to modify the refractive index of the IOL material, a signal from the IOL is measured to determine the processing effect (Continued)

of the refractive index modification, and based on the determination, to adjust the laser system parameters to achieve intended processing result. The signal measured from the IOL may be a fluorescent signal induced by the treatment laser, a fluorescent signal induced by an external illumination source, a temporary photodarkening effect, a color change, or a refractive index change directly measured by phase stabilized OCT.

17 Claims, 6 Drawing Sheets

(52) U.S. Cl.
CPC ............... *A61B 2017/00061* (2013.01); *A61B 2017/00154* (2013.01); *A61F 2009/00844* (2013.01); *A61F 2009/00851* (2013.01); *A61F 2009/00897* (2013.01); *A61L 2430/16* (2013.01)

(56) References Cited

U.S. PATENT DOCUMENTS

| | | |
|---|---|---|
| 2010/0082017 A1 | 4/2010 | Zickler et al. |
| 2012/0310223 A1* | 12/2012 | Knox .................. A61F 9/00827 606/5 |
| 2013/0158531 A1* | 6/2013 | Goldshleger ....... A61F 9/00825 606/6 |
| 2013/0289543 A1* | 10/2013 | Mordaunt ........... A61F 9/00838 606/5 |
| 2015/0221125 A1* | 8/2015 | Shimizu ............... A61B 3/1015 382/128 |
| 2015/0335477 A1 | 11/2015 | Schuele et al. |
| 2016/0128558 A1* | 5/2016 | Larin .................. A61B 5/0093 351/205 |
| 2018/0200112 A1* | 7/2018 | Krampert ............. A61B 3/1005 |
| 2019/0021904 A1 | 1/2019 | Schuele et al. |
| 2019/0307554 A1 | 10/2019 | Schuele et al. |

* cited by examiner

PROCESS MONITORING AND CONTROL DURING LASER-BASED REFRACTIVE INDEX MODIFICATION OF INTRAOCULAR LENSES IN PATIENTS

CROSS-REFERENCES TO RELATED APPLICATIONS

This application is a U.S. national stage of and claims the benefit under 35 U.S.C. § 371 of International Patent Application No. PCT/IB2020/053327, filed Apr. 7, 2020, which claims priority to U.S. Provisional Application Nos. 62/925,185, filed Oct. 23, 2019 and 62/832,797, filed Apr. 11, 2019, all of which are incorporated herein by reference in their entirety.

BACKGROUND OF THE INVENTION

Field of the Invention

This invention relates to a laser-based process of changing refractive properties of an implanted intraocular lens (IOL) by modification of the refractive index the IOL material, and in particular, it relates to process monitoring a control during laser-based in situ refractive index modification.

Description of Related Art

Despite all optimizations in modern pre-surgical diagnostic and IOL formula optimization, about 30% of cataract patients are left with visually significant refractive error after cataract surgery. This may include spherical and cylindrical power misses but also misses in matching existing higher order aberrations like chromatic aberrations. These misses—the mismatches between the required optical power and the actual resulting optical power of the IOL—can be corrected post cataract surgery by modifying the lens using a laser. For example, post-surgical shape correction of the IOL by UV photo cross linking and the resulting shape change has been demonstrated and commercialized, for example, by RxSight, Inc.

For laser applications in human eye tissues which are sensitive to intensity of the laser, variability of transmission through the tissues is an important factor that affects treatment outcome. For example, in a post-surgical IOL modification process, variability in optical transmission can play an important role, especially considering the transmission of the cornea in an aged person in the case of exposure of intraocular implantable devices. Reduced transmission of the laser through the cornea results in a less effective treatment. The commercially available system of RxSight solves this by applying multiple exposure settings to hit the final intended target refraction.

SUMMARY

The present invention is directed to a method and related apparatus for in situ modification of the refractive index of an IOL that substantially obviates one or more of the problems due to limitations and disadvantages of the related art.

An object of the present invention is to provide non-invasive monitoring of the desired laser treatment process to ensure optimized and reliable treatment outcome. More specifically, an object of the present invention is to provide a method to monitor the process of altering the intraocular lens while it is processed in situ.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides a method for real-time process monitoring during laser-based refractive index modification of an intraocular lens (IOL), which includes: treating the IOL with a laser beam to modify a refractive index of a material of the IOL; while treating the IOL with the laser beam, measuring a signal from the IOL to determine a processing effect of the refractive index modification; and based on the determination, further treating the IOL with a laser beam. The signal measured from the IOL may be a fluorescent signal caused by the treatment laser, a fluorescent signal caused by an external illumination source, a temporary photodarkening effect, a color change, or a refractive index change directly measured by phase stabilized OCT.

It is to be understood that both the foregoing general description and the following detailed description are exemplary and explanatory and are intended to provide further explanation of the invention as claimed.

DETAILED DESCRIPTION OF PREFERRED EMBODIMENTS

Commonly owned, co-pending U.S. patent application Ser. No. 16/375,784, filed Apr. 4, 2019, entitled Methods and Systems for Changing a Refractive Property of an Implantable Intraocular Lens ("the '784 application"), describes a "method of altering a refractive property of a crosslinked acrylic polymer material by irradiating the material with a high energy pulsed laser beam to change its refractive index. The method is used to alter the refractive property, and hence the optical power, of an implantable intraocular lens after implantation in the patient's eye. In some examples, the wavelength of the laser beam is in the far red and near IR range and the light is absorbed by the crosslinked acrylic polymer via two-photon absorption at high laser pulse energy . . . . The method can be used to form a Fresnel lens in the optical zone [of the IOL]." (Abstract.) As described in the '784 application, the IOL may be formed of a crosslinked acrylic polymer, and the refractive index modification is achieved through heating of the material. The laser beam may be a femtosecond pulsed laser emitting in the blue range, or the red and near infrared range, in which case the IOL material absorbs the laser light through two-photon absorption. The content of the '784 application is incorporated herein by reference in its entirety.

In such a method, the effectiveness of the laser in inducing a refractive index change in the IOL material is a function of laser power. As discussed earlier, variability in optical transmission of the laser beam through the patient's cornea can significantly affect the laser beam power that reaches the IOL, especially considering the variability transmission of the cornea in an aged person.

Figure 2:
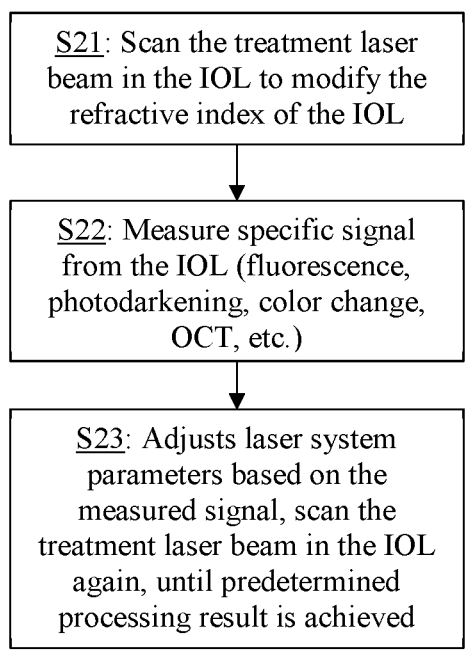
FIG. 2 schematically illustrates an ophthalmic laser surgical method according to embodiments of the present invention.

To solve this problem, embodiments of the present invention provide methods for real-time process monitoring of the modification of the IOL, based on different underlying mechanisms. While the IOL is processed with the laser beam, a specific signal from the IOL is measured and compared to the intended signal. A control system then adjusts laser system parameters to drive the system to the intended result. The overall process is summarized in FIG. 2.

More specifically, during a laser-based refractive index modification procedure of an implanted IOL, the treatment laser beam is scanned in the IOL to modify the refractive index of the IOL material at selected locations (step S21). While the IOL is processed with the laser beam, a specific signal from the IOL (e.g., fluorescence, photodarkening, color change, OCT, etc.) is measured (step S22). Based on the measured signal, one or more parameters of the treatment laser system are adjusted and the treatment laser beam is again scanned in the IOL (step S23). Steps S22 and S23 are repeated until predetermined processing result of the IOL is achieved.

Here, "while the IOL is processed with the laser beam" means when the patient's eye is continuously coupled to the laser system. The monitoring may occur concurrently with the laser beam scanning in the IOL, or between different laser beam scans of the treatment plan, or after the scans according to the treatment plan are completed but the laser system is still coupled to the patient's eye. All of these scenarios are referred to as real-time process monitoring.

An advantage of the process monitoring method is that the treatment process may be automatically adjusted to achieve the desired outcome in situ. Multiple treatments (i.e., releasing the patient's eye from the laser system after an IOL modification procedure, and performing another IOL modification procedure at a later time) are not required.

Figure 1:
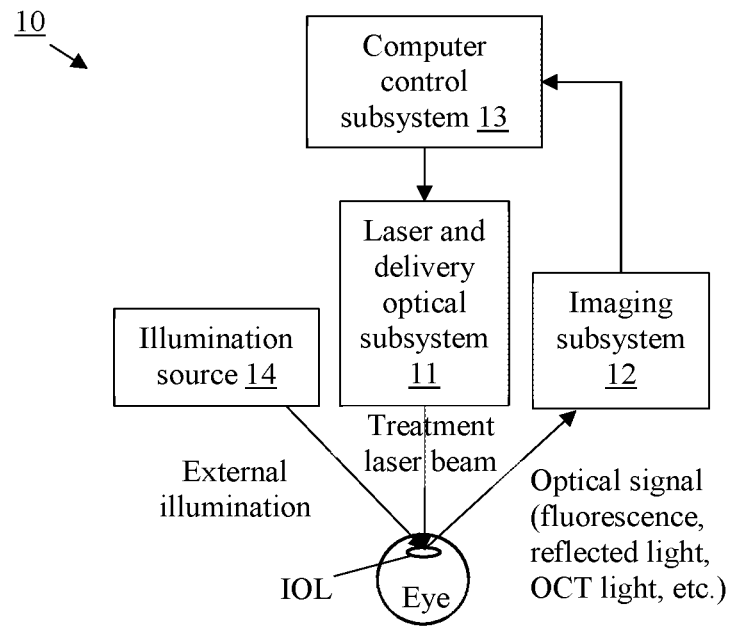
FIG. 1 schematically illustrates an ophthalmic laser surgical system in which embodiments of the present invention may be implemented.

FIG. 1 schematically illustrates an ophthalmic laser surgical system 10 in which embodiments of the present invention may be implemented. The system 10 includes a laser device and associated beam delivery optical subsystem 11 for delivering a pulsed laser beam to the eye for treatment, an imaging subsystem 12 for detecting a signal from the eye, and a computer control subsystem 13 that performs control and data processing functions. In some embodiments, the system 10 also includes an external illumination source 14. The imaging subsystem 12 may be implemented by different devices in the different embodiments described below. Although not shown in FIG. 1, the imaging subsystem 12 and the beam delivery optical subsystem 11 may share certain optical components in some embodiments. Many types of ophthalmic laser surgical system are known in the art and their detailed descriptions are omitted here. For example, commonly owned U.S. Pat. No. 8,845,625, which is incorporated herein by reference in its entirely, discloses in its FIGS. 1-4 and accompanying descriptions in the specification, an ophthalmic laser surgical system that includes an ultrafast laser source, a beam delivery optical subsystem including scanning devices, an OCT subsystem, an imaging subsystem such as a video monitoring subsystem for viewing an image of the eye, an aim beam subsystem, and related control subsystem.

In a first embodiment of the present invention, during in situ laser treatment of the IOL to modify the refractive index of the IOL material, while the treatment laser beam is scanned in the IOL, the treatment laser induced fluorescence (which may be referred to as autofluorescence) of the IOL material is measured and used as an indicator of the effectiveness of the laser induced processing of the IOL. The fluorescence signal can then be used to automatically adjust the treatment laser and optical subsystem 11 and perform further treatment so as to achieve the intended treatment outcome. Monitoring may be achieved by the imaging subsystem 12 which may use a video camera of the ophthalmic laser surgical system or a separate detector which is optimized for the detection of the induced fluorescence.

Figure 3:
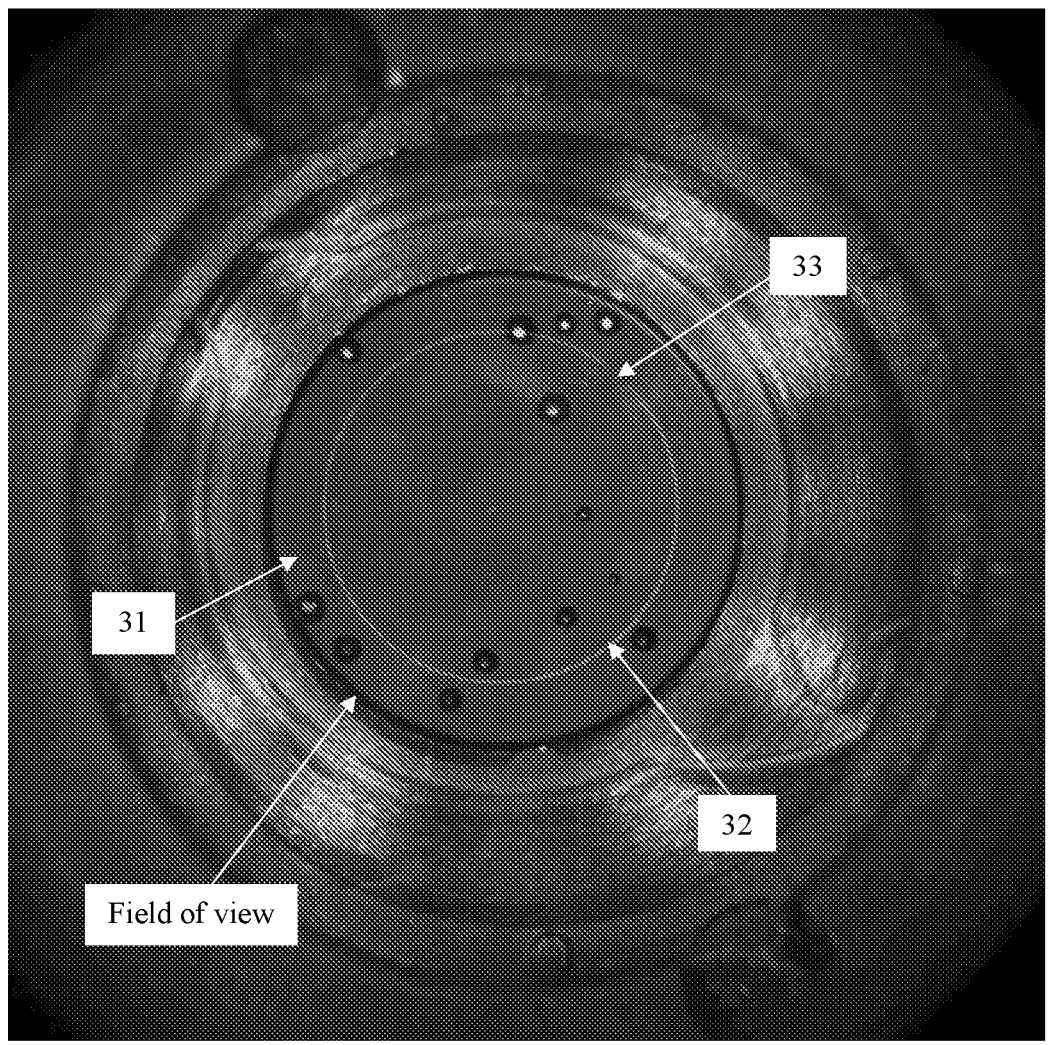
FIGS. 3-7 are examples of signals obtained from the IOL in real time according to various embodiments of the present invention.

FIG. 3 shows an example of the aforementioned process monitoring conditions which allow optimization of the laser treatment process. This example shows the fluorescence signal 32 in the IOL material 31 induced by irradiation of the femtosecond treatment laser. The more the IOL material is processed by the laser power (i.e. the more change in the refractive index of the IOL material), the higher the fluorescence intensity. In this example, the treatment laser scans a series of circular patterns in the IOL, and this image shows a specific diameter range which is irradiated during the integration time of the video frame. Note that since autofluorescence lasts a relatively short time, other portions of the laser scan pattern are substantially not visible in the video image. Such images allow the visualization of the fluorescence, and further, the optimization of the treatment process based on the measured fluorescence intensity.

In this example, the expected fluorescence signal is a circle with uniform intensity. In the exemplary image shown in FIG. 3, however, there is a visible gap (a missing short streak) 33 in the top right corner of the florescence ring 32, which indicates incomplete processing of the IOL material at that location. This may be due to, for example, an overlying bubble on the glass interface of the part of the optical system that contacts the patient's eye (the patient interface). In response to such observed gaps of the scan pattern, the laser system may be adjusted to perform additional processing at that location. In other examples (not shown), variations of the fluorescence intensity along the laser beam scan path may indicate variations in the transmission of the cornea. In response to such observed intensity variation, parts of the laser scan pattern may be repeated to achieve more uniform processing. Further, fluorescence intensity of different scan patterns, such as different rings, may be compared, and the laser system may be adjusted accordingly in response to such measurements and comparison, for example, to repeat some scan patterns that previously produced relatively weak fluorescence.

The positions and shape of the detected fluorescence pattern in the image may also be used to determine whether laser processing occurred at intended locations of the IOL material.

Thus, the autofluorescence signal of this embodiment may be used to monitor the refractive index modification procedure to achieve desired goals such as: (1) The shape of the scan pattern should be symmetrical or otherwise as intended. For example, the ring pattern should be centrally symmetrical or have other desired shape such as an oval shape for astigmatism correction. Errors in this respect should be corrected. (2) The scan lines should have no gap. If gaps are present, which may be due to absorption or scattering by the eye tissue or bubbles formed by the treatment laser, additional scanning (touching up) may be performed to fill the gaps.

Moreover, the relationship between the fluorescence intensity induced by a laser scan and the amount of resulting refractive index change in the IOL material caused by the same laser scan may be measured to obtain a calibration relationship between the two. A relationship between the measured fluorescence intensity and the corresponding laser parameters (e.g. laser pulse energy) may also be established as a calibration relationship. When establishing such calibration relationships, other factors of the laser system that affect the measured fluorescence intensity should be taken into consideration.

In a second embodiment of the present invention, during in situ laser treatment of the IOL, an external fluorescence illumination source 14 (different from the treatment laser 11) is used to illuminate the IOL to induce fluorescence, which allows visualization of the fluorescence signal as indicator of the effectiveness of the laser induced processing of the IOL. The illumination (excitation) light wavelength may be optimized to maximize the efficacy of light conversion. The external illumination source 14 may be LEDs with an appropriate wavelength, or a secondary external laser light source with an appropriate wavelength. A wide range of excitation wavelengths are usable. Preferably, the excitation wavelengths are in the UV-blue spectrum range, and more preferably, between 360-410 nm. The imaging subsystem 12 may be a video camera of the ophthalmic laser surgical system or a separate detector optimized for the detection of the induced fluorescence.

Figure 4:
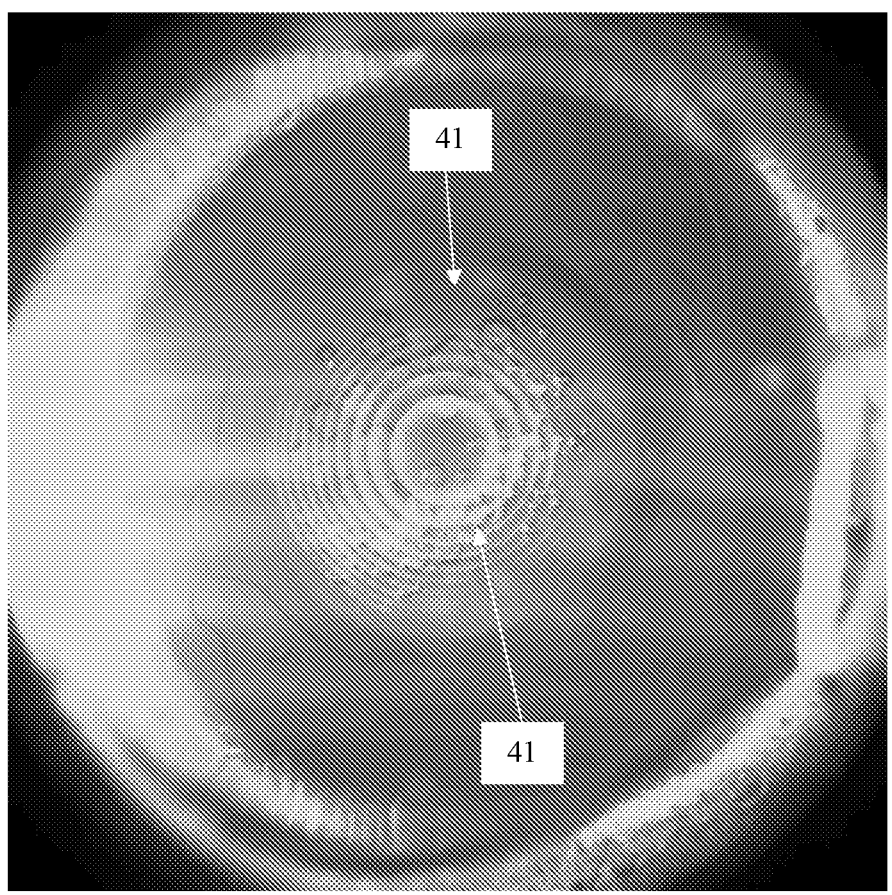

FIG. 4 shows an example of a processed IOL 41 under illumination with a UV or blue wavelength laser source (e.g., 405 nm). The processed areas show increased fluorescence on the ring like phase structure 42 of a Fresnel-type lens structure. As described in the above-referenced '784 application, by scanning the laser beam in the IOL in concentric ring patterns, concentric rings of refractive index variation may be generated, forming a Fresnel lens. The fluorescence is stronger at locations with increased processing effect of the IOL material. In this image, the radially varying processing effect can be seen. Note here that this image is taken after multiple rings of the Fresnel-type lens structure have been formed, and all rings formed thus far are seen, which is different from autofluorescence image of the first embodiment where only the ring being scanned is seen. The observed fluorescence intensity or intensity variation may be used as guidance of the IOL processing. For example, as seen in this image, the lower-left portion of the Fresnel-type lens structure has more and stronger rings than other portions, which may indicate that the refractive index modification was not spatially uniform. In response, further processing of the IOL material may be performed to correct the spatial nonuniformity. During the IOL refractive index modification process, multiple such fluorescence images (snapshots) may be taken from time to time to evaluate the effect of the laser processing. Preferably, the external illumination light 14 is turned on only when the fluorescence images are being taken, although it is also possible to keep the illumination light on throughout the procedure.

In addition to achieving the goals (1) and (2) described above, the fluorescence signal measured in the second embodiment may be used to achieve the following additional goals: (3) The different rings of the Fresnel-type lens structure should have desired relative amounts of laser processing. (4) The radial profile of refractive index modification in the IOL should be as intended for forming the Fresnel lens, such as a sawtooth shaped profile. Errors in these respects may be corrected by additional laser scans.

In some alternative embodiments, the imaging of the fluorescence signal may be combined with imaging of the IOL under a white light illumination, using the same imaging camera. The images under the white light illumination can reveal bubbles in the IOL material formed by the treatment laser. In one particular embodiment, a first image with only the white light illumination is taken before treatment laser scans, and a second image (or images) with both the white light illumination and the UV-blue light illumination is taken after some laser scans. The first image is subtracted from the second image to obtain a difference image, which contains both bubbles generated by the laser scan and the fluorescence signal indicating the amount of refractive index change in the IOL material.

Figure 5:
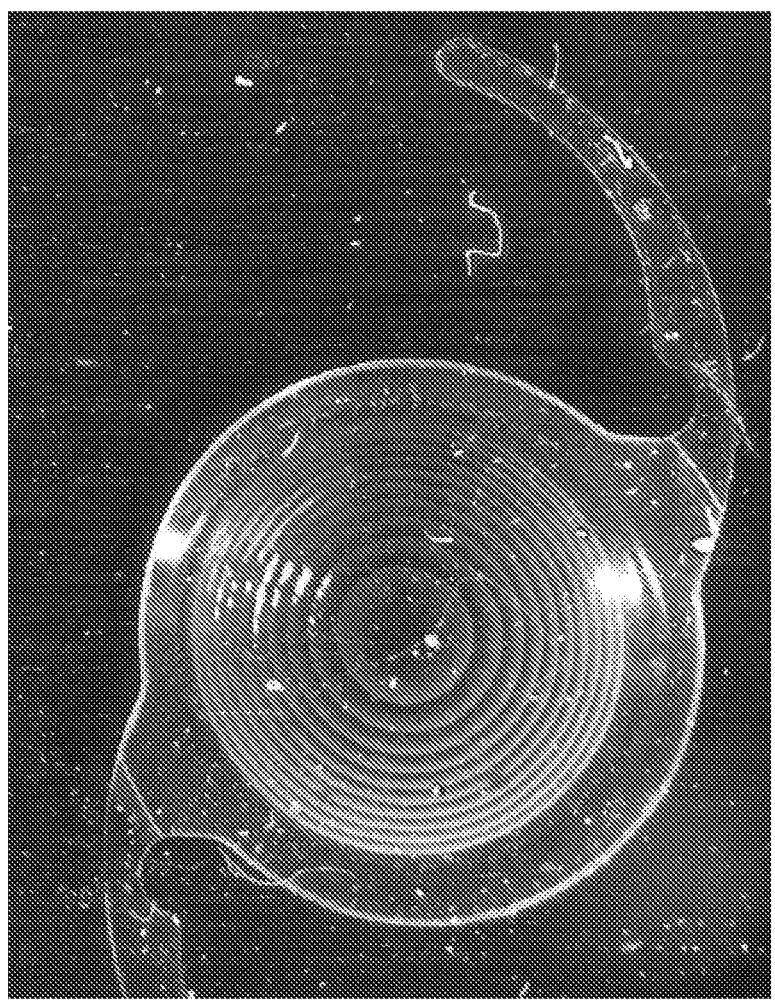

Similarly, FIG. 5 shows a processed IOL under illumination with a UV LED flash light (365 nm). Similar to FIG. 4, the processed areas in this image show increased fluorescence on the ring like phase structure of a Fresnel-type lens structure.

When taking fluorescence images using an external fluorescence illumination source, care should be taken to account for or eliminate artifacts caused by the illumination angle. For example, in the image of FIG. 5, it is possible that the angular nonuniformity in the fluorescence intensity of the rings is due to the illumination angle.

In a third embodiment of the present invention, during in situ laser treatment of the IOL, a temporary photodarkening effect, which is an effect of the chemical processing of the IOL, may be utilized as a process monitoring parameter. Preferably, retro-illumination (illumination from behind the IOL by light reflected from other structures of the eye) is used to produce images with better contrast. The more the refractive index change achieved in the IOL, the more the material will be darkened. The video camera (the imaging subsystem 12) of the ophthalmic laser system may be used to visualize and measure photodarkening effect as an indicator of the effectiveness of the laser induced processing of the IOL. Based on the observed photodarkening effect, the laser system may be adjusted and further treatment performed so as to correct possible transmission induced variances.

Figure 6:
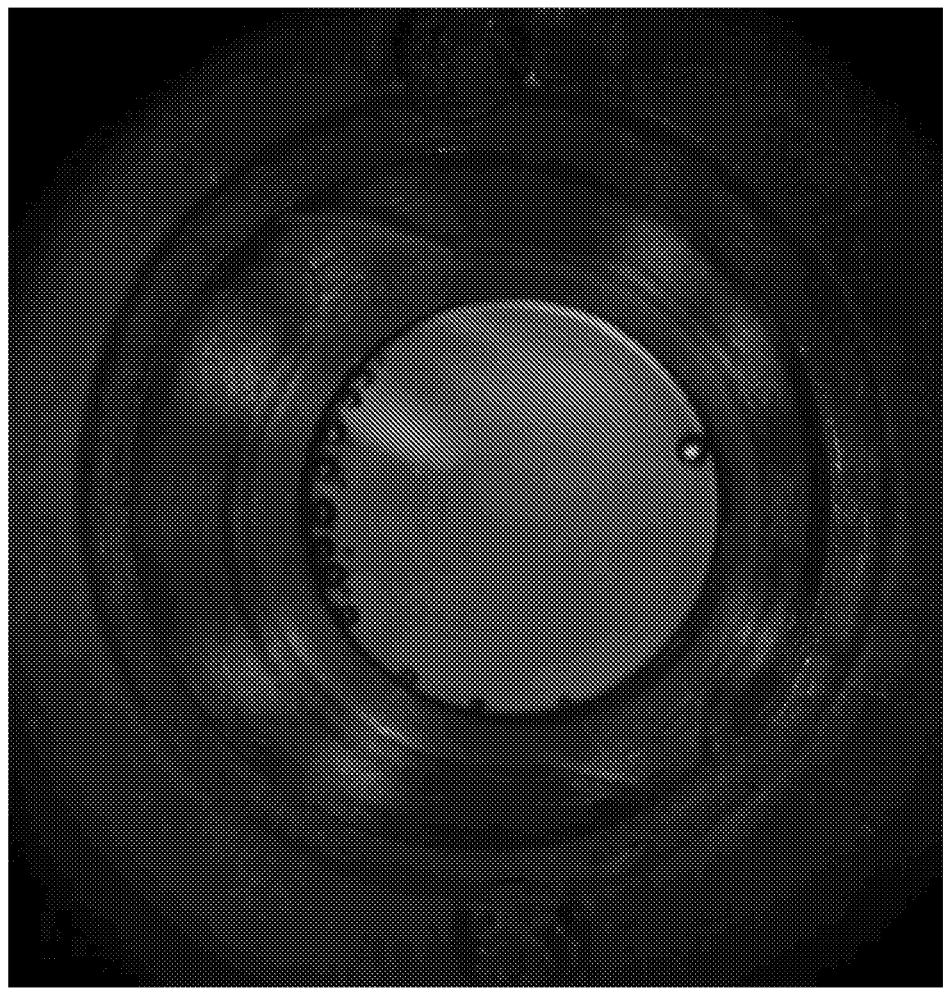

FIG. 6 shows the photodarkening during processing of the IOL with the femtosecond laser. With retro illumination, the Fresnel like structure of the pattern written in the IOL is clearly visible.

In a fourth embodiment of the present invention, during in situ laser treatment of the IOL, color changes in the IOL induced as a result of the treatment process may be used as an indicator of the effectiveness of the treatment. An external broadband light source is used to illuminate the IOL. The color change in the IOL may be correlated with the induced refractive index change of the IOL material in an in vitro calibration process. The color change measured during the treatment process may then be used as an indicator of the refractive index change achieved and then used to control the treatment process. The video camera of the ophthalmic laser system may be used as the imaging subsystem 12 to visualize and measure color change effect.

Figure 7:
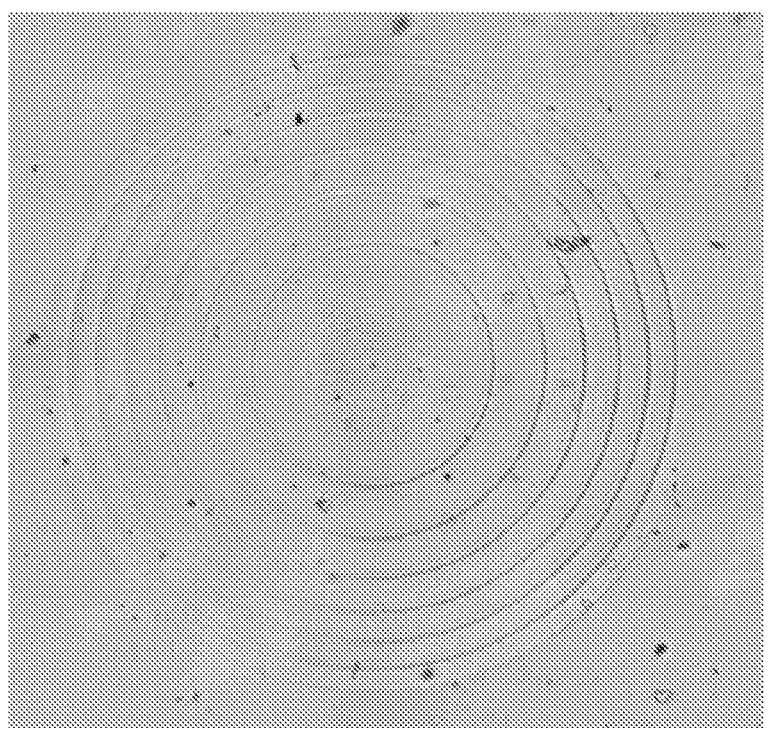

FIG. 7 shows the color change caused by the processing of the IOL with the laser beam. With the illumination, the color change between the Fresnel structure of the pattern written in the IOL is clearly visible.

The color change may be measured by the changes in ratios of the red (R), green (G) and blue (B) pixel values of the color image obtained by the video camera, for example, the ratio of R to B or the ratio of G to B. Other measures of color change may be used, such as by measuring a spectral shift.

The fluorescence-based, color change and the photodarkening methods described above can monitor the chemical alterations of the IOL material. These observed signals are not direct measures of the refractive index change, but are measures of IOL properties that are a proxy for the desired refractive index change. In some embodiments, calibrations may be performed to relate these material changes to a refractive index change achieved in the material. In such embodiments, by monitoring the refractive index change in the material during treatment, the result of the treatment process can be compared with the intended refractive index change and the treatment process can be controlled to achieve the desired outcome.

In a fifth embodiment of the present invention, during in situ laser treatment of the IOL, phase stabilized swept-source OCT is used to directly monitor the induced refractive index change in the IOL. It has been observed that the refractive index change in the IOL is small immediately after the treatment, but additional refractive index change occurs over a period of time such as hours or days after treatment, resulting in the final, desired refractive index change. Therefore, the phase stabilized swept-source OCT measurements during the treatment process can be correlated with long term outcomes in a clinical trial. The OCT measurements performed during the treatment process may then be used to control the treatment process to achieve the desired long term outcome using this correlation.

The above described methods of monitoring treatment process, in particular the fluorescence signal detection method, may be applied to other ophthalmic procedures, such as LASIK refractive surgery.

It will be apparent to those skilled in the art that various modification and variations can be made in the method and related apparatus for real-time process monitoring during laser-based refractive index modification of an IOL of the present invention without departing from the spirit or scope of the invention. Thus, it is intended that the present invention cover modifications and variations that come within the scope of the appended claims and their equivalents.

What is claimed is:

1. A method for real-time process monitoring during laser-based refractive index modification of an intraocular lens (IOL), comprising:
    treating the IOL with a laser beam to modify a refractive index of the IOL at selected locations;
    while treating the IOL with the laser beam:
        illuminating the IOL with an external illumination source which is different from the laser beam, wherein the IOL generates a fluorescent signal in response to the illumination, the fluorescent signal being induced by the illumination and indicative of a refractive index change of the IOL;
        measuring an image of the fluorescent signal from the IOL; and
        determining a processing effect of refractive index modification of the IOL based on the measured image of the fluorescent signal; and
    based on the determination, further treating the IOL with the laser beam.

2. The method of claim 1, wherein the laser beam is a femtosecond pulsed laser beam.

3. The method of claim 1, wherein the IOL is formed of a crosslinked acrylic polymer.

4. The method of claim 1,
    wherein the step of treating the IOL with the laser beam includes scanning the laser beam in a scanning pattern having multiple concentric rings in the IOL,
    wherein the step of determining a processing effect of refractive index modification of the IOL includes detecting a plurality of concentric rings of the fluorescent signal in the measured image and detecting any non-uniformity of intensity of the fluorescent signal in an angular direction along the plurality of concentric rings of the fluorescent signal, and
    wherein the step of further treating the IOL with the laser beam includes scanning the laser beam within the IOL in selected portions of the multiple concentric rings of the scanning pattern.

5. The method of claim 1, wherein the step of further treating the IOL with the laser beam includes adjusting one or more parameters of the laser beam.

6. A method for real-time process monitoring during laser-based refractive index modification of an intraocular lens (IOL), comprising:
    treating the IOL with a laser beam to modify a refractive index of the IOL at selected locations;
    while treating the IOL with the laser beam:
        illuminating the IOL with an external illumination source which is different from the laser beam, wherein the IOL generates a temporary photodarkening effect in response to the illumination, the temporary photodarkening effect being indicative of a refractive index change of the IOL;
        measuring the temporary photodarkening effect in an image of the IOL; and
        determining a processing effect of refractive index modification of the IOL based on the measured temporary photodarkening effect in the image; and
    based on the determination, further treating the IOL with the laser beam.

7. The method of claim 6, wherein the laser beam is a femtosecond pulsed laser beam and the IOL is formed of a crosslinked acrylic polymer.

8. The method of claim 6, wherein the step of further treating the IOL with the laser beam includes adjusting one or more parameters of the laser beam.

9. The method of claim 6, wherein the step of treating the IOL with the laser beam to modify a refractive index of the IOL at selected locations includes scanning the laser beam in a scanning pattern having multiple concentric rings in the IOL,
    wherein the step of determining a processing effect of refractive index modification of the IOL includes detecting a plurality of concentric rings in the measured image and detecting any non-uniformity of intensity of the image in an angular direction along the plurality of concentric rings, and
    wherein the step of further treating the IOL with the laser beam includes scanning the laser beam within the IOL in selected portions of the multiple concentric rings of the scanning pattern.

10. A method for real-time process monitoring during laser-based refractive index modification of an intraocular lens (IOL), comprising:
    treating the IOL with a laser beam to modify a refractive index of the IOL at selected locations;
    while treating the IOL with the laser beam:
        illuminating the IOL with an external illumination source which is a broadband visible light source and different from the laser beam, wherein the IOL generates a color change in response to the illumination, the color change being indicative of a refractive index change of the IOL;
        measuring the color change in an image of the IOL; and
        determining a processing effect of refractive index modification of the IOL based on the measured color change in the image; and based on the determination, further treating the IOL with the laser beam.

11. The method of claim 10, wherein the laser beam is a femtosecond pulsed laser beam and the IOL is formed of a crosslinked acrylic polymer.

12. The method of claim 10, wherein the step of further treating the IOL with the laser beam includes adjusting one or more parameters of the laser beam.

13. The method of claim 10, wherein the step of treating the IOL with the laser beam to modify a refractive index of the IOL at selected locations includes scanning the laser beam in a scanning pattern having multiple concentric rings in the IOL, wherein the step of determining a processing effect of refractive index modification of the IOL includes detecting a plurality of concentric rings in the measured image and detecting any non-uniformity of color of the image in an angular direction along the plurality of concentric rings, and wherein the step of further treating the IOL with the laser beam includes scanning the laser beam within the IOL in selected portions of the multiple concentric rings of the scanning pattern.

14. A method for real-time process monitoring during laser-based refractive index modification of an intraocular lens (IOL), comprising:

treating the IOL with a laser beam to modify a refractive index of the IOL at selected locations, including scanning the laser beam along at least one circular pattern in the IOL;

while treating the IOL with the laser beam, measuring an image of a fluorescent signal from the IOL, the fluorescent signal being induced by the treatment laser beam and indicative of a refractive index change of the IOL; and determining a processing effect of refractive index modification of the IOL based on the measured image, including detecting at least one circular pattern of the fluorescent signal in the measured image and detecting any non-uniformity of intensity of the fluorescent signal in an angular direction along the circular pattern of the fluorescent signal; and based on the detected non-uniformity of intensity, further treating the IOL with the laser beam.

15. The method of claim 14, wherein the laser beam is a femtosecond pulsed laser beam and the IOL is formed of a crosslinked acrylic polymer.

16. The method of claim 14, wherein the step of further treating the IOL with the laser beam includes adjusting one or more parameters of the laser beam.

17. The method of claim 14, wherein the step of further treating the IOL with the laser beam includes scanning the laser beam within the IOL in selected portions of the circle.

* * * * *